United States Patent
Senni et al.

(10) Patent No.: US 9,125,883 B2
(45) Date of Patent: Sep. 8, 2015

(54) SULFATED DEPOLYMERIZED DERIVATIVES OF EXOPOLYSACCHARIDES (EPS) FROM MESOPHILIC MARINE BACTERIA, METHOD FOR PREPARING SAME, AND USES THEREOF IN TISSUE REGENERATION

(71) Applicants: INSTITUT FRANCAIS DE RECHERCHE POUR L'EXPLOITATION DE LA MER (IFREMER), Issy les Moulineaux (FR); UNIVERSITE RENE DESCARTES PARIS 5, Paris Cedex (FR)

(72) Inventors: Karim Senni, Aulnay-sous-Bois (FR); Farida Gueniche, Rueil-Malmaison (FR); Myriam Yousfi, Paris (FR); Florence Fioretti, Paris (FR); Gaston-Jacques Godeau, Antony (FR); Sylvia Colliec-Jouault, Nantes (FR); Jacqueline Ratiskol, Sainte Luce sur Loire (FR); Corinne Sinquin, Nantes (FR); Gérard Raguenes, Locmaria Plouzane (FR); Anthony Courtois, Saint Renan (FR); Jean Guezennec, Plouzane (FR)

(73) Assignees: INSTITUT FRANCAIS DE RECHERCHE POUR L'EXPLOITATION DE LA MER (IFREMER), Issy les Moulineaux (FR); UNIVERSITE RENE DESCARTES PARIS 5, Paris (FR)

( * ) Notice: Subject to any disclaimer, the term of this patent is extended or adjusted under 35 U.S.C. 154(b) by 0 days.

(21) Appl. No.: 14/052,133

(22) Filed: Oct. 11, 2013

(65) Prior Publication Data
US 2014/0037597 A1 Feb. 6, 2014

Related U.S. Application Data

(62) Division of application No. 12/986,820, filed on Jan. 7, 2011, which is a division of application No. 11/629,579, filed as application No. PCT/FR2005/001379 on Jun. 6, 2005, now abandoned.

(30) Foreign Application Priority Data

Jun. 14, 2004 (FR) .................................. 04 06405

(51) Int. Cl.
*A61K 31/737* (2006.01)
*C12N 5/0775* (2010.01)
*A61K 35/28* (2015.01)
*C08B 37/00* (2006.01)

(52) U.S. Cl.
CPC ............... *A61K 35/28* (2013.01); *A61K 31/737* (2013.01); *C08B 37/006* (2013.01); *C12N 5/0675* (2013.01)

(58) Field of Classification Search
CPC ..................................................... A61K 31/737
USPC ............................................................ 514/54
See application file for complete search history.

(56) References Cited

U.S. PATENT DOCUMENTS

| 4,102,566 | A | 7/1978 | Shelton |
| 5,771,086 | A | 6/1998 | Horikawa et al. |
| 5,847,800 | A | 12/1998 | Tachibana et al. |
| 6,250,755 | B1 | 6/2001 | Conner et al. |
| 6,436,680 | B1 | 8/2002 | Guezennec et al. |
| 6,545,145 | B1 | 4/2003 | Rougeaux et al. |
| 6,828,307 | B1 | 12/2004 | Colliec-Jouault et al. |
| 7,015,206 | B2 | 3/2006 | Guezennec et al. |
| 2002/0076810 | A1* | 6/2002 | Radice et al. ................. 435/325 |
| 2005/0069518 | A1 | 3/2005 | Mousa et al. |

(Continued)

FOREIGN PATENT DOCUMENTS

| EP | 0 221 977 | 5/1987 |
| EP | 0 975 791 | 2/2000 |

(Continued)

OTHER PUBLICATIONS

Strauer, B. E. et al., Circulation, "Repair of Infarcted Myocardium by Autologous Intracoronary Mononuclear Bone Marrow Cell Transplantion in Humans", 2002, vol. 106, pp. 1913-1918.*

(Continued)

*Primary Examiner* — Shaojia Anna Jiang
*Assistant Examiner* — Bahar Craigo
(74) *Attorney, Agent, or Firm* — Marshall, Gerstein & Borun LLP

(57) ABSTRACT

The invention relates to certain low-molecular weight sulphated polysaccharide derivatives of marine native exopolysaccharides (EPSs) excreted by mesophilic marine bacteria from a deep hydrothermal environment, wherein said derivatives can be obtained by means of a method which comprises a step of free radical depolymerization of said native EPSs followed by a step of sulphating the resulting depolymerized derivatives. The present invention further relates to the use of said low-molecular weight sulphated polysaccharide derivatives as a wound-healing agent, particularly for preparing pharmaceutical compositions suitable for treating or preventing diseases of the connective tissues and particularly skin and gum tissues. The figure demonstrates how polysaccharide derivative GY 785 DRS according to the invention can stimulate fibroblast proliferation in latticed or reconstructed connective tissues at a concentration of 10 μg (m) g/ml.

18 Claims, 6 Drawing Sheets

(56) References Cited

U.S. PATENT DOCUMENTS

2005/0245736 A1 11/2005 Oreste et al.
2005/0256079 A1 11/2005 Oreste et al.
2006/0014718 A1 1/2006 Oreste et al.

FOREIGN PATENT DOCUMENTS

| FR | 2 701 488 | 8/1994 |
|---|---|---|
| FR | 2 755 142 | 4/1998 |
| JP | 10-218902 | 8/1998 |

OTHER PUBLICATIONS

Senni, Karim et al., Marine Drugs, "Marine Polysaccharides: A Source of Bioactive Molecules for Cell Therapy and Tissue Engineering", Sep. 2011, vol. 9, pp. 1664-1681.*
"Fibrosis", DermNet NZ, definition on p. 1 of 6. Available at <URL:http://dermnetnz.org/pathology/pathology-glossary.html>, last viewed Nov. 1, 2011.
"Keloids", The Merck Manual Professional. Available at <URL:http://www.merckmanuals.com/professional/dermatologic_disorders/benign_skin_tumors/keloids.html?qt=keloid&alt=sh>, last viewed Nov. 2, 2011.
"Prevent", WordNet Search—3.0. Available at <URL:http://wordnetweb.princeton.edu/perl/webwn>, last viewed Nov. 2, 2011.
Aymard et al., Rheological properties in aqueous media of three new bacterial polysaccharides from marine origin. Food Hydrocoll. 5: 167-9 (1991).
Belcher et al., The determination of glucosamine. Analyst. 79: 201-8 (1954).
Bozzi et al., Characterization and solution properties of a new exopolysaccharide excreted by the bacterium *Alteromonas* sp. strain 1644. Int. J. Biol. Macromol. 18: 9-17 (1996).
Cambon-Bonavita et al., A novel polymer produced by a bacterium isolated from a deep-sea hydrothermal vent polychaete annelid. J. App. Microbio., 93: 310-315 (2002).
Chevolot et al., Further data on the structure of brown seaweed fucans: Relationship with anticoagulant activity. *Carbohydrate Res.*, 319: 154-65 (1999).
Colliec Jouault et al., Characterization, chemical modifications and in vitro anticoagulant properties of an exopolysaccharide produced by *Alteromonas infernus*. Biochim. Biophys. Acta. 1528: 141-51 (2001).
Dubreucq et al., Structure determination of a novel uronic acid residue isolated from the properties of an exopolysaccharide produced by a bacterium originating from deep sea hydrothermal vents. Carbohydr. Res. 290: 175-81 (1996).
Elson et al., A colorimetric method for the determination of glucosamine and chondrosamine. Biochem. J. 27: 1824-8 (1933).
Filisetti-Cozzi et al., Measurement of uronic acids without interference from neutral sugars. *Anal. Biochem.* 197: 157-62 (1991).
Guezennec et al., Preliminary chemical characterization of unusual eubacterial exopolysacchrides of deep-sea origin. *Carbohydr. Polym.* 24: 287-94 (1994).
Guezennec et al., Sulfation and depolymerization of a bacterial exopolysaccharide of hydrothermal origin. *Carbohydr. Polym.*, 37: 19-24 (1998).
Guezennec, Deep-sea hydrothermal vents: A new source of innovative bacterial exopolysaccharides of biotechnological interest? *J. Ind. Microbio. Biotech.*, 29: 204-208 (2002).
Holmstrom et al., Marine *Pseudoalteromonas* Species are Associated with Higher Organisms and Produce Biologically Active Extracellular Agents, *FEMS Microbiology Ecology*, 30:285-293 (1999).
International Search Report, European Patent Office, PCT/FR2005/001379, dated Mar. 1, 2006.
Kamerling et al., Characterization by gas-liquid chromatography-mass spectrometry and proton-magnetic-resonance spectroscopy of pertrimethylsilyl methyl glycosides obtained in the methanolysis of glycoproteins and glycopeptides. *Biochem. J.* 151: 491-5 (1975).
Li et al., Angiogenesis in wound healing. *Contemporary Surgery: Supplemental to Contemporary Surgery.* pp. 1-36, Nov. 2003.
Matou et al., Effect of an oversulfated exopolysaccharide on angiogenesis induced by fibroblast growth factor-2 or vascular endothelial growth factor in vito, Biochemical Pharmacology, 69(2):751-759 (2005).
Merriam-Webster Online Dictionary "derivative". Available at <URL:http://www.merriam-webster.com/dictionary/derivative>, retrieved Jul. 15, 2009.
Montreuil et al., Glycoproteins In: Carbohydrate analysis, a practical approach. IRL Press, Oxford, Chapter 5: 143-204 (1986).
Nema et al., Excipients and Their Use in Injectable Products, PDA Journal of Pharmaceutical Science & Technology, 51(4):166-171 (1997).
Nishino et al., Anticoagulant and antithrombin activities of oversulfated fucans. *Carbohydrate Res.*, 229: 355-62 (1992).
O'Leary et al., Fucoidan modulates the effect of transforming growth factor (TGF)-beta1 on fibroblast proliferation and wound repopulation in in vitro models of dermal wound repair, Biol. Pharm. Bull., 27(2):266-270 (2004).
Raguenes et al., *Alteromonas infernus* sp. A novel, new polysaccharide-producina bacterium isolated from a deep-sea hydrothermal vent. *J. App. Microbio.*, 82: 422-430 (1997).
Raguenes et al., Description of a new polymer-secreting bacterium from a deep-sea hydrothermal vent, *Alteromonas macleodii* subsp. fijiensis, and preliminary characterization of the polymer. *Appl. Env. Microbiol.* 62: 67-73 (1996).
Raguenes et al., Novel highly viscous polysaccharide excreted by an *Alteromonas* isolated from a deep-sea hydrothermal vent shrimp. *Curr. Microbio.*, 46: 448-452 (2003).
Raguenes et al., *Vibrio diabolicus* sp. A novel, new polysaccharide-secreting organism isolated from a deep-sea hydrothermal vent polychaete annelid, *Alvinella pompejana*. Int. J. Syst. Bacteriol.. 47: 989-95 (1997).
Rimington, The carbohydrate complex of the serum proteins: Improved method for isolation and re-determination of structure. Isolation of glucosaminodimannose from proteins of ox blood. *Biochem. J.* 25: 1062-71 (1931).
Roger et al., Structural studies of the main exopolysaccharide produced by the deep-sea bacterium *Alteromonas infernus*. *Carbohydr. Res.* 339: 2371-2380 (2004).
Rougeaux et al., Novel bacterial exopolysaccharides from deep-sea hydrothermal vents. *Carbohydr. Polym.* 31: 237-42 (1996).
Rougeaux et al., Structural determination of the exopolysaccharide of *Pseudoalteromonas* strain HYD 721 isolated from a deep-sea hydrothermal vent. *Carbohyd. Res.* 315: 273-285 (1999).
Rougeaux et al., Structural studies of an exopolysaccharide produced by *Alteromonas macleodii* subsp. *fijiensis* originating from a deep-sea hydrothermal vent. *Carbohyd. Res.* 312: 53-59 (1998).
Rougeaux et al., Structure of the exopolysaccharide of *Vibrio diabolicus* isolated from a deep-sea hydrothermal vent. *Carbohydr. Res.* 322: 40-5 (1999).
Vincent et al., Production and characterization of an exopolysaccharide excreted by a deep-sea hydrothermal vent bacterium isolated from the polychaete annelid *Alvinella pompejana*. Appl. Environ. Microb. 60: 4134-41 (1994).
Wiechelman et al., Investigation of the bicinchoninic acid protein assay: identification of the groups responsible for color formation. *Anal. Biochem.* 175: 231-7 (1988).
Zanchetta et al., A new bone-healing material: A hyaluronic acid-like bacterial exopolysaccharide. *Calcif. Tissue Int.*, 72:74-79 (2003).
Zou et al., Oligosaccharide fragments of the tyoe III group B *streptococcal* polysaccharide derived from *S. pneumoniae* type 14 capsular polysaccharide by a chemoenzymatic method. *Carbohyd. Res.* 309: 297-301 (1998).
Zubkov et al., Structure of the capsular polysaccharide from *Alteromaonas* sp. CMM 155. *Carbohydr. Res.* 275: 147-54 (1995).

* cited by examiner

-Magnifications: a and b 13; c and d 26, e and f 52
-Immunodetection of α -SMA and counter-staining with hemalin)
▶Isolated myofibroblast, ▶Myofibroblast terminal differentiation

SULFATED DEPOLYMERIZED DERIVATIVES OF EXOPOLYSACCHARIDES (EPS) FROM MESOPHILIC MARINE BACTERIA, METHOD FOR PREPARING SAME, AND USES THEREOF IN TISSUE REGENERATION

CROSS-REFERENCE TO RELATED APPLICATIONS

This application is a divisional of U.S. Ser. No. 12/986,820, filed Jan. 7, 2011, which is a divisional of U.S. Ser. No. 11/629,579, filed Dec. 13, 2006, which is the U.S. National Phase of PCT/FR2005/001379, filed Jun. 6, 2005, which claims the benefit of French Patent Application No. 0406405, filed Jun. 14, 2004.

The present invention relates to polysaccharide derivatives obtained from native polysaccharides of a specific type, called exopolysaccharides (EPSs) that are excreted by various strains of mesophilic marine bacteria from a deep hydrothermal environment.

More particularly, the present invention relates to low-molecular-weight highly sulfated polysaccharide derivatives that can be obtained by free-radical depolymerization and sulfation of exopolysaccharides.

Highly sulfated low-molecular-weight polysaccharides that are not bacterial exopolysaccharide derivatives are already known. They have advantageous properties, in particular as therapeutic substances. For example, heparin, a sulfated polysaccharide, is the anticoagulant and antithrombotic agent most commonly used in the prevention and treatment of venous thrombosis. The commercially available heparins are currently extracted from porcine intestinal mucosa. However, the use of these heparins of animal origin presents a risk of contamination with pathogenic agents (for example, prion). In order to reduce or avoid the risk of contamination, the identification of novel polysaccharides from origins other than animal origins appears to be a particularly promising line of research.

Polysaccharides from bacteria, and more particularly from marine bacteria, make it possible to satisfy this need. The study and exploitation of polysaccharides excreted by marine bacteria, or exopolysaccharides, therefore falls within this line of research, in particular for the design of novel active ingredients or of analogs of already existing molecules.

A screening of samples derived from the hydrothermal environment of the ocean depths has made it possible to isolate a large variety of mesophilic bacterial strains capable of producing native EPSs at atmospheric pressure and at ambient temperature.

A small number of native EPSs has already been the subject of patent filings and of publications: for example, European patent EP 975 791 describes the strain *Vibrio diabolicus*, the native EPS HE 800 and the use thereof as a medicament, including, in particular, as a retroviral, antitumor and antithrombotic agent. In the native state, the EPS HE 800, of 800 000 g/mol, is not sulfated; it consists of approximately 30% by weight of amino sugar, 32% by weight of acid monosaccharides and 1% by weight of neutral monosaccharides; its protein content is close to 1% by weight. European patent application No 1 296 695 describes the use of the EPS HE 800 in its native form as a material for facilitating bone healing (Zanchetta et al., *Calcif Tissue Int.*, 2003, 72: 74-79).

A second native EPS, called GY 785 and produced by the bacterium *Alteromonas infernos*, has also been identified and described in French patent No. 2 755 142. The native EPS GY 785 consists of a heterogeneous population of polysaccharide chains having an average molar mass of greater than $10^6$ g/mol. The native EPS GY 785 is slightly sulfated (amount of sulfate less than 10% by weight); it consists of 57% by weight of neutral monosaccharides (predominantly glucose and galactose) and 42% by weight of acidic monosaccharides (glucuronic acid and galacturonic acid); it does not comprise any amino sugars or acetate, lactate, pyruvate and succinate substituents; its protein content is approximately 4% by weight (Guezennec J., *Ind. Microb. Biotech.*, 2002, 29: 204-208).

A third native EPS, called ST 716 and produced by the bacterium *Alteromonas macleodii* subsp. *fijiensis* has also been identified and described in European patent EP 1171625 (Rougeaux H. et al., *Carbohydr. Res.*, 1998, 312: 53-59). The native EPS ST 716 is slightly sulfated (its amount of sulfate is approximately 5% by weight); it consists of 40% by weight of neutral monosaccharides and 40% of acidic monosaccharides; its protein content is 2 to 4% by weight.

Other novel native EPSs have also been identified and described in the literature; in particular, the EPS HYD 721 produced by a *Pseudoalteromonas* (Rougeaux H. et al., *Carbohydr. Res.*, 1999, 315: 273-285 and Raguenes G. et al., 1997), the EPS HYD 657 (Carnbon-Bonavita M. et al., *J. Applied Microbiol*, 2002, 93: 310-315) and the EPS MS 907 (Raguenes G. et al., *Curr. Microbiol*, 2003, 46: 448-52).

A subject of the present invention is sulfated polysaccharide derivatives that come from the treatment of native EPSs excreted by mesophilic bacterial strains from a deep hydrothermal environment and that are of pharmaceutical or cosmetic value or of value in tissue engineering. The sulfated polysaccharide derivatives of native exopolysaccharides (EPSs) excreted by mesophilic marine bacteria from a deep hydrothermal environment according to the invention can be obtained by means of the method comprising the following steps:

a step consisting of free-radical depolymerization of said native EPSs, so as to obtain depolymerized derivatives of low molecular weight, less than or equal to 100 g/mol, a subsequent step consisting of sulfation of the optionally lyophilized, depolymerized derivatives, comprising the addition of at least one sulfation agent in a sufficient amount to obtain sulfated polysaccharide derivatives having a degree of sulfate-group substitution of between 10% and 45% by weight relative to the total weight of the sulfated polysaccharide derivative, said sulfation step being optionally followed by a dialysis step.

During the first depolymerization step, the native EPS can be used in a liquid form, i.e. as it is excreted by the bacteria into the culture medium. Preferably, the culture medium is centrifuged and only the supernatant containing the native EPS and free of bacterial debris is conserved. The native EPS can be collected by any suitable technique known to those skilled in the art, in particular by membrane ultrafiltration, and can then optionally be lyophilized as it is or in the form of an addition salt.

The step consisting of free-radical depolymerization of the native EPS is preferably carried out by addition of a solution of an oxidizing agent to a reaction mixture comprising the native EPS, preferably in the presence of a metal catalyst. The oxidizing agent is preferably chosen from peroxides, in particular hydrogen peroxide, and peracids, in particular peracetic acid and 3-chloroperbenzoic acid. The addition is preferably carried out continuously and with stirring for a period of between 30 minutes and 10 hours. Reaction mixture is preferably maintained at a pH of between 6 and 8, for example by continuous addition of a basifying agent such as sodium hydroxide, and at a temperature of between approximately 30 and 70° C. throughout the duration of the free-radical depolymerization reaction.

According to a specific embodiment of the present invention, in this step, the native EPS is present in the reaction mixture at a concentration of between approximately 2 and 10 mg/ml of reaction mixture.

According to a preferred embodiment of the invention, the oxidizing agent is a solution of hydrogen peroxide ($H_2O_2$) preferably having a concentration of between approximately 0.1% and 0.5% by weight, preferably of the order of 0.1% to 0.2% by weight, which is added at a flow rate of V1/1000 to V1/10 ml/minute, preferably V1/50 and V1/500 ml/minute, very preferably of the order of V1/100 ml/minute, V1 being the volume of the reaction medium containing a marine exopolysaccharide (EPS) to which a solution of hydrogen peroxide is added.

The metal catalysts that can be used during the depolymerization step are preferably chosen from $Cu^{++}$, $Fe^{++}$ and $Cr^{+++}$ ions and the $Cr_2O_7^{2-}$ anion, as described in particular in patent application EP 0 221 977. According to a specific embodiment, the metal catalyst is present in the reaction mixture at a concentration of between approximately $10^{-3}$ M and $10^{-1}$ M, and preferably at a concentration of between approximately 0.001 and 0.05 M.

The free-radical depolymerization process in accordance with the invention and as described above makes it possible to obtain, in a single step, without fractionation by stearic exclusion chromatography, and with a good yield, homogeneous, low-molecular-weight polysaccharide derivatives. The term "low-molecular-weight polysaccharide derivatives" is intended to mean derivatives with a molecular weight of less than or equal to 100 000 g/mol, preferably between 5000 and 50 000 g/mol, and more preferably less than or equal to 25 000 g/mol. In the context of the disclosure of the present invention, the term "homogeneous derivatives" is intended to mean derivatives which, by high performance stearic exclusion chromatography, exhibit a single main peak representing a predominant population of polysaccharide chains that are homogeneous with respect to size, characterized by a polydispersity index I (Mw/Mn)<5, preferably of between 1.5 and 4, more preferably less than or equal to 2, with Mw=weight-average molecular weight and Mn=number-average molecular weight.

When the depolymerization reaction has finished, according to a specific embodiment of the invention, the process comprises a step consisting of reduction of the polysaccharide derivatives obtained, using a reducing agent, so as to stabilize the chains, the reducing ends of which are very reactive, and in particular so as to avoid chain hydrolysis by the "peeling" reaction. The nature of the reducing agents that can be used to this effect is not essential. It may in particular be sodium borohydride.

The metal catalyst used for the depolymerization can be eliminated at the end of the depolymerization reaction, and in the embodiment in which a reduction step is carried out, at the end of the reduction, by ion exchange chromatography, preferably a weak cation exchange resin passivated beforehand, or by treatment with EDTA (ethylenediaminetetraacetic acid).

According to a specific embodiment of the process of the invention, prior to the sulfation step, a step consisting of N-deacetylation of the polysaccharide derivatives comprising N-acetylated hexosamines and obtained at the end of the free-radical depolymerization step and/or at the end of the reduction step is carried out. This N-deacetylation step is carried out according to a protocol adapted from Zou et al. (Carbohyd. Res., 1998, 309: 297-301). Advantageously, the N-deacetylation step is carried out by addition, to the reaction mixture comprising the polysaccharide derivatives, of a solution of sodium borohydride, with stirring. When the temperature of the reaction mixture reaches approximately 80° C., a basifying agent, preferably sodium hydroxide, is added to the reaction medium. The mechanism of basic hydrolysis of an amide in a basic medium, and preferably in the presence of sodium hydroxide, is shown schematically below:

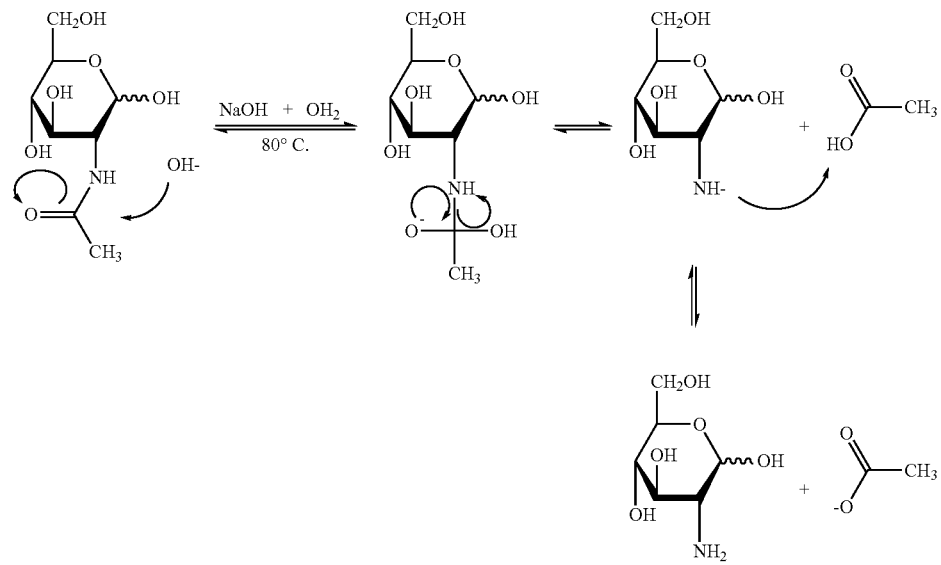

After reaction for one hour, the reaction medium is neutralized by continuous addition of acetic acid until a pH of 5 is obtained. The polysaccharide derivatives obtained can be recovered by membrane ultrafiltration and then can optionally be lyophilized.

According to a preferred embodiment, the N-deacetylation step is carried out on the polysaccharide derivatives originating from the depolymerization of native EPSs excreted by hydrothermal mesophilic marine bacteria of the *Vibrio* genus, preferably HE 800. The native EPSs excreted by said bacteria of the *Vibrio* genus are characterized in that they contain N-acetylated hexosamines.

The polysaccharide derivatives resulting from the depolymerization and/or from the reduction and/or from the N-deacetylation can, if necessary, be recovered by any suitable technique well known to those skilled in the art, such as, for example, by membrane ultrafiltration, and then can optionally be lyophilized as they are or in the form of an addition salt with a weak or strong base, that may, for example, be chosen from pyridine, triethylamine, tributylamine, tetrabutylammonium hydroxide and sodium hydroxide. This lyophilized salt may, for example, be prepared by elution of an aqueous solution of the polysaccharide derivatives at a concentration of between 1 and 8 mg/ml on an ion exchange resin column such as, for example, those sold under the name Dowex® by the company Dow Chemical. The eluate is collected as long as the pH remains acid, for example less than 5, then the pH is subsequently adjusted to approximately 6.5 with the desired base as defined above. The polysaccharide derivatives in the form of a salt are then ultrafiltered and lyophilized.

The lyophilized polysaccharide derivatives, possibly in the form of an addition salt, are preferably dissolved in an anhydrous solvent at the beginning of the sulfation step; this solvent is preferably chosen from dimethylformamide (DMF), dimethyl sulfoxide (DMSO) and/or formamide. The amount of polysaccharide derivatives present in the anhydrous solvent may be between approximately 1 and 10 mg/ml, preferably between approximately 1 and 5 mg/ml, and even more preferentially this amount is approximately 2.5 mg/ml. The dissolution of the EPS in the anhydrous solvent is preferably carried out, with stirring, at ambient temperature for approximately 1 to 2 hours and then at a temperature of between 40 and 50° C., preferably at a temperature of approximately 45° C. for approximately 2 hours under argon with molecular sieve.

The chemical sulfation agent(s) used during the sulfation step can be added to the depolymerized and/or reduced and/or N-deacetylated EPSs that are in lyophilized form or in the form of a solution.

The sulfation agents are preferably chosen from complexes of pyridine sulfate (free or coupled to a polymer), of dimethylformamide sulfate, triethylamine sulfate and of trimethylamine sulfate. The chemical sulfation agent(s) is (are) added to the solution of polysaccharide derivatives in a weight amount preferably representing from approximately 4 to 6 times, and even more preferably approximately 5 times, the mass of polysaccharide derivatives in solution. The chemical sulfation reaction is then preferably carried out with stirring for a period of between approximately and 24 hours depending on the desired degree of sulfation. When the desired degree of sulfation is reached, the sulfation reaction is stopped after cooling of the reaction medium:
- either by addition of water in a proportion preferably equal to ¹⁄₁₀ of the reaction volume and adjustment of the pH of the reaction medium to 9 with a basifying agent such as, for example, sodium hydroxide (3 M);
- or, and preferably, by precipitation in the presence of sodium-chloride-saturated acetone or of methanol, and then dissolution of the precipitate in water.

According to a specific embodiment, the solution of sulfated polysaccharide derivatives is preferably dialyzed in order to remove the various salts, and then lyophilized.

In the context of the invention, the term "sulfated polysaccharide derivatives" is intended to mean polysaccharide derivatives that have been subjected to a chemical sulfation treatment and comprise sulfate groups, irrespective of whether or not they have sulfate groups before this sulfation treatment.

Preferably, the low-molecular-weight sulfated polysaccharide derivatives in accordance with the invention have a molecular weight of less than or equal to 100 000 g/mol, preferably of between 5000 and 50 000 g/mol, a polydispersity index of less than 5, preferably of between 1.5 and 4, and a degree of sulfate group substitution of between 10% and 45% by weight, and preferably of between 20% and 40% by weight, inclusive.

More preferably, the low-molecular-weight sulfated polysaccharide derivatives in accordance with the invention have a molecular weight of less than or equal to 25 000 g/mol, a polydispersity index of less than 2, and a degree of sulfate-group substitution of between 10% and 45% by weight, and preferably of between 20% and 40% by weight, inclusive.

According to a preferred embodiment of the invention, the low-molecular-weight sulfated polysaccharide derivatives in accordance with the invention are obtained by treatment of native EPSs excreted by mesophilic marine bacteria of hydrothermal origin preferably belonging to the *Alteromonas* or *Vibrio* genus.

According to a variant of the invention, the bacteria of the *Alteromonas* genus are selected from the strains GY 785, HYD 657, HYD 721, HYD 1545, HYD 1644, ST 716 and MS 907.

The invention relates to low-molecular-weight sulfated polysaccharide derivatives obtained from native EPSs excreted by bacteria of the *Alteromonas* genus, said native EPSs having a neutral monosaccharide content of from 20% to 70%, preferably from 30% to 60%, and more preferably from 38% to 57% by weight.

The invention also relates to low-molecular-weight sulfated polysaccharide derivatives obtained from native EPSs excreted by bacteria of the *Alteromonas* genus, said native EPSs having an acidic monosaccharide content of from 5% to 60%, preferably of between 6% and 50%, and more preferably of between 8% and 42% by weight.

The invention also relates to low-molecular-weight sulfated polysaccharide derivatives obtained from native EPSs excreted by bacteria of the *Alteromonas* genus, said native EPSs having an amino sugar content of from 0% to 1% by weight in their oside composition.

According to a specific embodiment, the low-molecular-weight sulfated polysaccharide derivatives of the invention are obtained from native EPSs excreted by bacteria of the *Alteromonas* genus, said native EPSs having an oside composition comprising:
- from 20% to 70%, preferably from 30% to 60%, and more preferably from 38% to 57% by weight of neutral monosaccharides,
- from 5% to 60%, preferably from 6% to 50%, and more preferably from 8% to 42% by weight of acidic monosaccharides,
- from 0% to 1% by weight of amino sugars.

According to another specific embodiment, the low-molecular-weight sulfated polysaccharide derivatives of the invention are obtained from native EPSs excreted by bacteria of the *Vibrio* genus, preferably by the bacterial strain HE 800. The native EPSs excreted by bacteria of the *Vibrio* genus are not sulfated.

The invention relates to low-molecular-weight sulfated polysaccharide derivatives obtained from native EPSs excreted by bacteria of the *Vibrio* genus, said native EPSs having a neutral monosaccharide content of from 0% to 5%, preferably from 0% to 1% by weight.

The invention relates to low-molecular-weight sulfated polysaccharide derivatives obtained from native EPSs excreted by bacteria of the *Vibrio* genus, said native EPSs having an acidic monosaccharide content of from 20% to 50%, preferably from 25% to 40%, and more preferably from 30% to 32% by weight.

The invention relates to low-molecular-weight sulfated polysaccharide derivatives obtained from native EPSs excreted by bacteria of the *Vibrio* genus, said native EPSs having an amino sugar content of from 20% to 50%, preferably from 25% to 40%, and more preferably from 30% to 35% by weight.

The invention relates to low-molecular-weight sulfated polysaccharide derivatives obtained from native EPSs excreted by bacteria of the *Vibrio* genus, said native EPSs having an N-acetylated group content of from 0% to 15%, preferably from 4% to 8%, and more preferably from 5% to 6% by weight.

According to a specific embodiment of the invention, the low-molecular-weight sulfated polysaccharide derivatives in accordance with the invention are characterized in that they are obtained from native EPSs excreted by bacteria of the *Vibrio* genus, said native EPSs having an oside composition comprising:

from 0% to 5%, preferably from 0% to 1% by weight of neutral monosaccharides,
from 20% to 50%, preferably from 25% to 40%, and more preferably from 30% to 32% by weight of acidic monosaccharides,
from 20% to 50%, preferably from 25% to 40%, and more preferably from 30% to 35% by weight of amino sugars,
from 0% to 15%, preferably from 4% to 8%, and more preferably from 5% to 6% by weight of N-acetylated groups.

The invention relates to low-molecular-weight sulfated polysaccharide derivatives obtained from native EPSs that have a protein content of from 0% to 15%, preferably from 0% to 5%, and more preferably from 0% to 1% by weight.

Surprisingly and unexpectedly, the inventors have demonstrated that the low-molecular-weight sulfated polysaccharide derivatives in accordance with the invention can be used as wound-healing agents for connective tissues, and are in particular capable of stimulating fibroblast proliferation, of inhibiting the secretion of pro-inflammatory cytokines or soluble mediators by fibroblasts, of inhibiting the secretion of matrix metalloproteases by fibroblasts, of inhibiting the conventional complement pathway, of stimulating the proliferation of fibroblasts to the detriment of myofibroblasts, and of selectively stimulating the proliferation of medullary cells intended to become mesenchymal cells to the detriment of other subpopulations in a heterogeneous population of cells.

Fibroblasts have a central role in the process of wound healing of a damaged tissue with a view to the formation of a replacement tissue so as to restore the functionality thereof. Typically, the wound-healing process takes place in 3 phases during which the fibroblasts cause the regeneration processes to progress according to chronological sequences that are precise but interlinked with one another:

(1) The first inflammatory and vascular wound-healing phase is characterized by the release of a large number of growth factors, of cytokines and of proteases and the migration of inflammatory cells, fibroblasts and vascular cells at the level of lesion. The influx of inflammatory cells and the production of cytokines induce the production of hydrolases such as serine proteases or matrix metalloproteases by the fibroblasts. When the inflammatory phase, which is normally transient, is uncontrollably prolonged, a chronic inflammatory pathology takes hold.

(2) The tissue reconstruction phase (proliferative phase or granulation tissue) is reflected by the loss of tissue substances that has occurred when there is a lesion being made up with an extracellular matrix that is relatively unorganized and richly vascularized. The fibroblasts proliferate rapidly under the effect of growth factors. These fibroblasts perform a remarkable job of reconstruction by secreting extracellular matrix components such as glycosaminoglycans (GAGs), fibronectin and collagen. Some of these fibroblasts acquires a myofibroblastic phenotype, expressing in particular smooth muscle α-actin. The cicatricial tissue retracts by virtue of the contractile capacities of the myofibroblasts.

(3) In the maturation phase, a large part of the myofibroblasts disappears due to apoptosis and is replaced with fibroblasts no longer expressing smooth muscle α-actin. At this stage, persistence of the myofibroblasts, by virtue of their activity, may lead to pathologies of fibrotic type. At the end of this process, a dense fibrous cicatricial tissue has been formed and can then remodel itself. The maturation of the cicatricial tissue is characterized in particular by a modification of the orientation of the matrix fibers, which tend to place themselves along lines of greater tension as in a normal connective tissue.

Tissue remodeling is a dynamic balance between the synthesis of the extracellular matrix and the degradation thereof. When this balance is in equilibrium, wound healing is normal. However, when the balance leans for a lengthy period toward extracellular matrix synthesis, the development of a fibrosis is witnessed. When the balance leans toward excessive degradation of the extracellular matrix, an inflammatory pathology takes hold.

The present invention relates to the use of the low-molecular-weight sulfated polysaccharide derivatives in accordance with the invention, as wound-healing agents for connective tissues, in particular dermal and gingival connective tissues.

Given the fact that the low-molecular-weight sulfated polysaccharide derivatives of the invention have fibroblast proliferation-activating properties, it is therefore particularly advantageous to use them as an agent capable of stimulating fibroblast proliferation, or as a regenerating agent for the preparation of a pharmaceutical composition with wound-healing activity, said composition making it possible in particular to promote the reconstruction and the remodeling of connective tissues, in particular of dermal and gingival connective tissues.

The inventors have also demonstrated that low-molecular-weight sulfated polysaccharide derivatives in accordance with the invention can be used as agents capable of inhibiting the secretion of pro-inflammatory cytokines or soluble mediators by connective tissue fibroblasts, including in particular interleukin 1β (IL-1β) and/or TNF-α (tumor necrosis factor).

Certain chronic inflammatory pathologies, such as periodontitis, chronic ulcers, delayed wound healing or rheumatoid arthritis, are accompanied by an excessive and uncontrolled degradation of matrix macromolecules. These pathologies are very often associated with the deleterious secretion of cytokines, in particular of pro-inflammatory cytokines, and with persistent activation of complement, resulting, inter alia, in the prejudicial overproduction of chemoattractant anaphylatoxins. In these inflammatory pathologies, the excessive production of pro-inflammatory cytokines disturbs the physiological cellular and tissue functions, including in particular cell migration, cell proliferation, and the expression, secretion and activation of certain proteases such as matrix metallproteases (MMPs). The expression of those MMPs involved in matrix protein degradation is not generally constitutive and is induced by pro-inflammatory cytokines such as IL-1β and/or TNF-α and/or growth factors.

The inventors have shown that the low-molecular-weight sulfated polysaccharide derivatives in accordance with the invention can be used as agents capable of inhibiting the secretion of matrix from metalloproteases by the fibroblasts of connective tissues, in particular of dermal and gingival connective tissues. In particular, the derivatives according to the invention are particularly effective for inhibiting the secretion of gelatinase A (MMP-2) and/or of stromelysine 1 (MMP-3). The inhibition of metalloprotease secretion has been demonstrated on fibroblasts irrespective of whether or not they are under the influence of pro-inflammatory cytokines such as IL-1β. It is in fact particularly advantageous to regulate the secretion of MMPs that may be responsible for the uncontrolled degradation of the matrix macromolecules in inflammatory pathologies affecting dermal and gingival connective tissues, including in particular periodontitis and chronic ulcerations.

By regulating pro-inflammatory cytokine and matrix metalloprotease secretion by connective tissue fibroblasts, and in particular dermal and gingival connective tissue fibroblasts, the sulfated polysaccharide derivatives in accordance with the invention show good anti-inflammatory activity.

Complement is a component of innate immunity (spontaneous activation in response to an attack) which is defined as a complex set of soluble or membrane proteins. When there is an inflammatory response, these proteins become activated in a series of proteolytic chain reactions that generates peptides with biological activities. Complement activation, which is rapid and localized, is subject to various particularly effective mechanisms of control. However, some of these control mechanisms are disturbed in inflammatory pathologies, such as autoimmune pathologies, leading to persistent complement activation. Surprisingly and unexpectedly, the inventors have demonstrated the use of the low-molecular-weight sulfated polysaccharide derivatives of the invention as agents capable of inhibiting the conventional complement pathway. Advantageously, the low-molecular-weight sulfated polysaccharide derivatives of the invention are used as anti-inflammatory agents for the preparation of a pharmaceutical composition for treating inflammatory pathologies in which complement is activated, in particular autoimmune pathologies, for instance pemphigus.

Given their anti-inflammatory properties, it is advantageous to use the low-molecular-weight sulfated polysaccharide derivatives of the invention as anti-inflammatory agents for the preparation of a pharmaceutical composition for in particular treating inflammatory pathologies of connective tissues, in particular of dermal and gingival connective tissues, for instance periodontitis, chronic ulcerations or delayed wound healing.

Many pathologies can bring about the appearance of an inflammatory process: not only autoimmune pathologies, but also neoplastic or infectious pathologies. Advantageously, the low-molecular-weight sulfated polysaccharide derivatives of the invention are used as anti-inflammatory agents for the preparation of a pharmaceutical composition for treating inflammatory pathologies affecting dermal and gingival connective tissues, in particular autoimmune, infectious or neoplastic pathologies, for instance sarcomas.

The development of pathological fibroses appears to follow a route similar to that followed during tissue regeneration. However, the normal control of the cellular functions that occur during tissue regeneration processes is disturbed. Specifically, imbalances in the cellular component can be reflected, inter alia, by an uncontrolled influx of inflammatory cells that maintain the tissue degradation and/or by the persistence of cell subpopulations such as myofibroblasts, leading to fibrotic pathologies. Whereas myofibroblasts appear transiently during normal wound-healing processes, this cell subpopulation persists when tissue regeneration becomes pathological.

The inventors have shown that the sulfated polysaccharide derivatives in accordance with the invention can be used as agents capable of stimulating the proliferation of fibroblasts to the detriment of myofibroblasts in connective tissues, in particular dermal and gingival connective tissues. More particularly, the sulfated polysaccharide derivatives in accordance with the invention can be used as agents capable of stimulating the proliferation of fibroblasts to the detriment of myofibroblasts in two-dimensional cell cultures or in reconstructed dermal and gingival connective tissues.

The use of the sulfated polysaccharide derivatives in accordance with the invention makes it possible to stimulate the proliferation of fibroblasts responsible for tissue homeostasis while at the same time controlling the persistence of myofibroblasts, two cellular events originating from the stimulation of the nonpathological process of tissue regeneration.

Given their property of selecting the fibroblast subpopulation to the detriment of the myofibroblast subpopulation, it is therefore particularly advantageous to use the low-molecular-weight sulfated polysaccharide derivatives as defined above, as anti-fibrotic agents for the preparation of a pharmaceutical composition, said composition making it possible, in particular, to prevent or treat hypertrophic wound-healing processes or fibrotic pathologies of connective tissues, in particular dermal and gingival connective tissues.

This property that the sulfated polysaccharide derivatives in accordance with the invention have of selecting a specific cell subpopulation within a heterogeneous population has also been exploited so as to promote the obtaining of a subpopulation of medullary cells intended to become mesenchymal cells. The medullary cells intended to become mesenchymal cells are adult stem cells capable of developing into differentiated mesenchymal cells depending on the tissue in which they find themselves, in particular into fibroblasts, chondrocytes, osteoblasts, adipocytes and muscle cells having specialized morphological characteristics and functions.

Thus, the inventors have demonstrated that the low-molecular-weight sulfated polysaccharide derivatives in accordance with the invention are capable of selectively stimulating the proliferation of medullary cells intended to become mesenchymal cells to the detriment of other subpopulations in a heterogeneous population of cells. This selective proliferative effect is all the more advantageous since medullary cells intended to become mesenchymal cells are rare since they are particularly difficult to obtain and to maintain in culture. It is therefore advantageous to complement cell culture media intended for the obtaining and maintaining of medullary cells intended to become mesenchymal cells, in the context of tissue or cell therapy.

Thus, the sulfated polysaccharide derivatives in accordance with the invention therefore allow a selection-amplification by proliferation of medullary cells intended to become mesenchymal cells. These medullary cells intended to become mesenchymal cells represent a source of pluripotent cells that can be used in tissue therapy for transplant purposes in humans, insofar as they are capable of differentiating into fibroblasts, chondrocytes, osteoblasts, adipocytes and muscle cells depending on the tissue in which they are implanted.

These cells are therefore advantageous in tissue and cell therapy and more particularly when it is impossible to take samples of skin fragments, as in individuals with third degree burns, or when the tissue no longer has the ability to regenerate, such as cartilage in adults.

Each of the pharmaceutical compositions or medicaments containing the low-molecular-weight sulfated polysaccharide derivatives obtained in accordance with the invention can also be used in combination with one or more growth factors present in the pharmaceutical composition or present in a different pharmaceutical composition that will then be administered separately, i.e. before, simultaneously, or after the administration of the pharmaceutical composition containing the sulfated polysaccharide derivatives. Such growth factors are in particular chosen from FGFs (fibroblast growth factors), TGFβs, BMPS (bone morphogenic proteins) and CTGF (connective tissue growth factor).

Given their properties on fibroblasts, the low-molecular-weight sulfated polysaccharide derivatives as defined above can be used for the preparation of a pharmaceutical composition with wound-healing and/or antifibrotic and/or anti-inflammatory activity.

The pharmaceutical compositions or medicaments of the invention are intended to be administered via the appropriate route. The pharmaceutical composition or the medicament of the invention is preferably in an injectable form, in which the sulfated polysaccharide derivatives have a molecular weight of between 5000 and 50 000 g/mol, preferably less than or equal to 25 000 g/mol, a polydispersity index of between 1.5 and 5, preferably less than or equal to 2, and a degree of sulfate group substitution of between 10% and 45%, and preferably between 20% and 40%, inclusive.

The present invention also relates to a cosmetic or dermatological composition, characterized in that it comprises low-molecular-weight sulfated polysaccharide derivatives in accordance with the invention, in combination with any suitable excipient.

Preferably, the pharmaceutical, cosmetic or dermatological compositions can be administered locally and can be in the form of a gel, a cream, an ointment, an emulsion or a solution.

They can also be used in situ by means of substrates, of medical devices that are resorbable or nonresorbable, such as, for example, delayed-release supports, slowly disintegrating sponges, or surgical implants.

The present invention will be understood more clearly from the examples that follow, which are read with regard to the attached figures; these examples are given only by way of illustration of the subject of the invention, of which they no way constitute a limitation.

FIG. 5 shows that the secretion of MMP-2 is inhibited;

EXAMPLE 1

Figure 1:
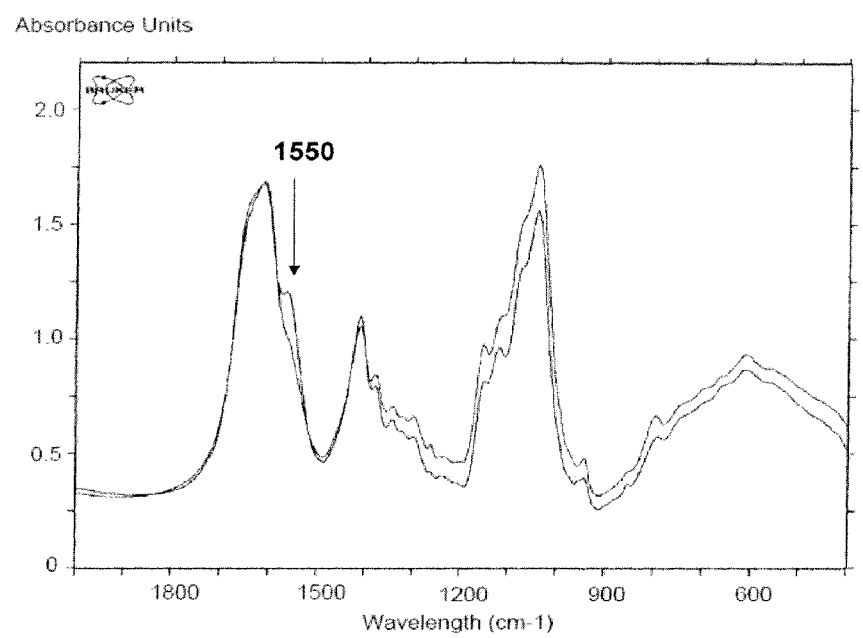
FIG. 1 is an infrared spectrum of the polysaccharide derivatives HE 800 that have undergone a free-radical depolymerization before (HE 800 DR) and after the N-deacetylation reaction (HE 800 DRN)

Oside Composition of the Bacterial Native EPSs

Methods:

The protein content was determined according to the ECA (bicinchoninic acid) method described by Wiehelman K. et al. (*Anal. Biochem.* 1988, 175: 231-237).

The neutral monosaccharide content was determined by the Tillmans and Philippi method (*Analyt. Chem.*, 1929, 28: 350) modified by Rimington (*Biochem. J.*, 1931, 25: 1062-1071).

The uronic acid (GlcA) content was established using a modification of the m-hydroxydiphenyl-$H_2SO_4$ method (Filisetti-Cozzi and Carpitta, *Anal. Biochem.*, 1991, 197: 157-162) and using glucuronic acid as standard. Interference from neutral hexoses was avoided by using potassium sulfamate and carrying out controls comprising all the reagents with the exception of the m-hydroxydiphenyl.

The neutral monosaccharide and acidic monosaccharide contents were determined by gas chromatography. The analysis of the glycoside residues in the form of trimethylsilylated derivatives was carried out according to the method of Kamerling et al. (*Biochem. J.*, 1975, 151: 491-495) and modified by Montreuil et al. (Glycoproteins In: Carbohydrate analysis, a practical approach, 1986, Chaplin M. F. and Kennedy J. F. (eds), IRL Press, Oxford, 143-204).

The hexosamine and N-acetylhexosamine (GalNAc and GlcNAC) content is determined by the method of Belcher et al. (*Analyst*, 1954, 79: 201-208) adapted from that of Elson and Morgan (*Biochem J.*, 1933, 27: 1824-1828) and using N-acetylglucosamine and glucosamine as standards.

The contents of total sulfates (free plus bound of the native EPSs) were determined by elemental analysis of sulfur (S %), and by applying the following relationship: percentage of sulfate groups (%)=3.22×S %. The amount of free sulfates is quantified by ion exchange chromatography on a Dionex® DX-500 system connected to a conductimeter, and according to the method described by the manufacturer Dionex. The result obtained makes it possible, to calculate the amount of sulfates really bound to the EPS derivative, which is equal to the amount of total sulfates (obtained by elemental analysis) minus the amount of free sulfates (obtained by ion exchange chromatography).

Description:

| Strain | EPS | OSIDE COMPOSITION | | | |
| --- | --- | --- | --- | --- | --- |
| | | Neutral % | Acid % | Amino sugars % | Sulfats % |
| HYD 1545[1, 2, 3] *Alteromonas* sp | 1545[1, 2, 3] | 49 | 34 | 0.2 | 11 |
| HYD 721[1, 2, 12] *Pseudoalteromonnas* sp | 721[1, 2, 12, 16] | 55 | 11 | <0.5 | 12 |
| HYD 1644[2, 7, 8] *Alteromonas* sp | 1644[2, 7, 8, 16] | 55 | 35 | <1 | 5 |

-continued

| Strain | EPS | OSIDE COMPOSITION | | | |
|---|---|---|---|---|---|
| | | Neutral % | Acid % | Amino sugars % | Sulfats % |
| HYD 657[2, 14] Alteromonas macleodii sp subsp fijiensis biovar deepsane | 657[2, 14] | 47 | 26 | 1.6 | 5 |
| ST 716[4, 9, 10] Alteromonas macleodii sp subsp fijiensis | 716[9, 10, 16] | 40 | 40 | <1 | 5 |
| GY 785[5] Alteromonas infernus sp | GY 785[5, 11, 15, 16] | 55 | 40 | <0.7 | 10 |
| MS 907[16] Alteromonas macleodii sp subsp fijiensis biovar medioatlantica | MS 907[16] | 50 | 37 | 0 | 0 |
| HE 800[6, 9, 13] Vibrio diabolicus sp | HE 800[6, 9, 13] | 1 | 32 | 30 | 0 |

[1](Aymard et al., 1991 *Food Hydrocoll*, 5, 167-169);
[2](Guezennec et al., 1994 *Carbohydr. Polym.*, 24, 287-294);
[3](Vincent et al., 1994 *Appl. Environ. Microb.*, 60, 4134-4141);
[4]Raguenes et al., 1996 *Appl. Env Microbiol*, 62, 67-73);
[5](Raguenes et al., 1997, *Journal of Systematic Bacteriology*, 47, 989-995);
[6](Raguenes et al., 1997 *J. Appl. Microbiol.*, 82, 422-430);
[7](Dubreucq et al., 1996 *Carbohydr. Res.*, 290, 175-81);
[8](Bozzi et al., 1996 *Int J. Biol. Macromol*, 18, 9-17);
[9](Rougeaux et al., 1996 *Carbohydr. Polym.* 31, 237-242);
[10](Rougeaux et al., 1998 *Carbohydr. Res.*, 312, 53-59);
[11](Guezennec et al., 1998 *Carbohydr. Polym.* 37, 19-24);
[12](Rougeaux et al., 1999 *Carbohydr Res.*, 315, 273-285);
[13](Rougeaux et al., 1999 *Carbohydr. Res.*, 322, 40-45);
[14]Cambon-Bonavita et al., 2002 *J Applied Microbiol*, 93, 310-315);
[15](Guezennec, 2002 *J Ind Microbiol Biol.*, 29, 204-208);
[16](Raguenes et al., 2003 *Curr Microbiol.*, 46, 448-52);
[17](Roger et al., 2004, *Res.*, 339, 2371-2380)

EXAMPLE 2

Preparation of Derivatives According to the Invention Based on the Native EPS HE 800

(1) HE 800 DR corresponds to the low-molecular-weight polysaccharide derivative,
(2) HE 800 DRS corresponds to the low-molecular-weight sulfated polysaccharide derivative,
(3) HE 800 DRNS corresponds to the low-molecular-weight N-deacetylated and sulfated polysaccharide derivative.

The low-molecular-weight sulfated polysaccharide derivatives in accordance with the invention are obtained: (i) for the DRS series, by applying a first step consisting of free-radical depolymerization (DR) and a sulfation step (S), and (ii) for the DRNS series, by applying a first step consisting of free-radical depolymerization (DR) followed by an N-deacetylation step (N) and a sulfation step (S).

2.1. Free-Radical Depolymerization of a Native EPS 500 mg of EPS from the marine bacterium of hydrothermal origin HE 800 are produced according to the process described in EP 975 791, and lyophilized. The native EPS is slowly rehydrated overnight in 100 ml of water and is introduced into a jacketed glass reactor. The metal catalyst is added to the reaction medium in the form of a solution of copper acetate at 16 mg/ml. The temperature of the medium is brought to 60° C. Magnetic stirring is maintained throughout the reaction. The reaction medium is brought to a pH of between 7.5 and 8 with 10N concentrated sodium hydroxide. The pH of the reaction medium is monitored and is regulated through the addition of a sodium hydroxide solution.

Hydrogen peroxide ($H_2O_2$) is then added to the reactor at a flow rate of 1 ml/min using a peristaltic pump. The hydrogen peroxide is prepared extemporaneously from a concentrated solution.

Reduction:

1 g of sodium borohydride per 1 g of polysaccharide derivative is dissolved in a small volume of water and then added directly to a reactor. The reaction takes place at ambient temperature and with stirring for a period of 2 to 20 hours. It is stopped by the addition of 10 N acetic acid. A blackish precipitate due to the copper forms during the reaction.

Elimination of the Catalyst:

In order to eliminate the precipitate formed during the reduction reaction, the solution containing the polysaccharide derivative is filtered through a büchner funnel equipped with filters made of 3 μm glass microfibers. The residual copper is then eliminated by passing the solution containing the polysaccharide derivative over a Chelex™ resin, with a capacity of 0.4 meq/ml. The solution containing the polysaccharide derivative percolates, at a flow rate of 4 to 5 ml/min, through a column (25×400 mm) of 200 ml of resin passivated beforehand. At the outlet, the solution containing the polysaccharide derivative has a basic pH of 10.

Diafiltration, Concentration by Ultrafiltration and Lyophilization:

The solution containing the polysaccharide derivative is ultrafiltered through a Pellicon 2 ultrafiltration system (Millipore) equipped with a Pall membrane of 1000 g/mol. The conductivity of the solution (4 to 5 mS) is measured throughout the diafiltration. When a stable value below 100 μS is reached on the filtrate, the solution is brought back to a neutral pH. It is then concentrated then lyophilized (CIRP lyophilizer). Once lyophilized, the polysaccharide derivative obtained is characterized.

2.2. N-Deacetylation

Principle:

With the aim of at once substituting the oside units in terms of N- and O-sulfate groups, the polysaccharide HE 800 DR is N-deacetylated. The process for N-deacetylation of the HE 800 derivative is carried out on large amounts of product.

Method:

259 mg of EPS HE 800 DR are solubilized in 10 ml of water and placed in a round-bottomed flask with magnetic stirring. 263 mg of $NaBH_4$ are solubilized in 1.25 ml of water and then added to the solution of EPS HE 800 DR. When the temperature of the mixture reaches 80° C., 1.25 ml of 10 N NaOH are added. The final concentration of the solution is then 1 N with respect to sodium hydroxide and 2% with respect to $NaBH_4$, for a total volume of 12.5 ml.

After reaction for one hour, the solution is neutralized with 10 N acetic acid until the effervescence has stopped. The volume added is 1.5 ml and the pH is 5. The solution is then ultrafiltered through a 1000 g/mol membrane and then lyophilized. 167 mg of N-deacetylated EPS HE 800 DR (HE 800 DRN) are obtained, reflecting a yield of 65%.

2.3. Sulfation of the EPS HE 800 DR or of HE 800 DRN

Preparation of the Polysaccharide in the Form of a Salt:

50 mg of EPS are solubilized in 20 ml of $H_2O$. The polysaccharide derivative is placed in the H+ form by elution on a Dowex resin column. The elution is carried out with water, and the eluate is collected as long as the pH remains acidic, preferably less than 5. The pH is immediately adjusted to 6.5 with the desired base (pyridine, triethylamine, tributylamine, sodium hydroxide). The polysaccharide derivative in the form of a salt is then lyophilized.

Sulfation of the Polysaccharide:

The polysaccharide derivative in the form of a salt is dissolved in 100 ml of anhydrous DMF with gentle stirring (250 rpm) for 2 hours at ambient temperature, and then for 2 hours at a temperature of 45° C.

When dissolution is complete, 2.5 g of pyridine-$SO_3$ complex are added to the reaction medium, i.e. 5 times the mass of the polysaccharide. The temperature of the mixture is then maintained at 45° C. for 2 hours with stirring. The reaction is terminated by adding 40 ml of water and sodium hydroxide in order to obtain a pH at 9. The reaction mixture is then dialyzed in water with a dialysis bag having a cutoff threshold of 3500 Da.

After dialysis, the solution containing the sulfated EPS is filtered through filters of 2.7 μm and 0.7 μm and ultrafiltered through a 1000 g/mol membrane and then lyophilized[2].

2.4. Characterization of the Various Derivatives:
(1) HE 800 DR; (2) HE 800 DRS and (3) HE 800 DRNS.

The molecular weights (Mc: chromatographic molecular weight determined at the summit of the peak; Mw: weight-average molecular weight and Mn: number-average molecular weight) and the polydispersity (I=Mw/Mn) of the various EPS HE 800 derivatives obtained were determined by high performance steric exclusion chromatography (HPSEC) on a Biotech system, in 0.1 M aqueous ammonium acetate at a flow rate of 0.1 ml/min using a Superdex® 200 column or a Superdex™ Peptide column (AMERSHAM). The column was calibrated with polysaccharide standards as follows: pullulans: 758 000-5900 g/mol (Polymer Laboratories, Interchim), noncommercial standard polysaccharides: 4000; 3000 and 1500 g/mol; melezitose: 522 g/mol (FLUKA), sucrose: 342 g/mol; glucose: 180 g/mol (SIGMA). The results are analyzed using the Aramis® software (Varian, France).

The neutral monosaccharide content was determined by the method of Tillmans and Philippi (*Analyt. Chem.*, 1929, 28, 350-) modified by Rimington (*Biochem. J.*, 1931, 25: 1062-1071).

The uronic acid (GlcA) content was established using a modification of the m-hydroxydiphenyl-$H_2SO_4$ method (Filisetti-Cozzi and Carpitta, *Anal. Biochem.*, 1991, 197: 157-162) and using glucuronic acid as standard. Interference from neutral hexoses was avoided by using potassium sulfamate and carrying out controls comprising all the reagents with the exception of the m-hydroxydiphenyl.

The hexosamine and N-acetylhexosamine (GalNAc and GlcNAc) content is determined by the method of Belcher et al. (*Analyst*, 1954, 79: 201-208) adapted from that of Elson and Morgan (*Biochem J.*, 1933, 27: 1824-1828) and using N-acetylglucosamine and glucosamine as standard.

The total sulfates (free plus bound) contents were determined by elemental analysis of sulfur (S %), and by applying the following relationship: percentage of sulfate groups (%)=3.22×S %.

The amount of free sulfates is quantified by ion exchange chromatography on a Dionex® DX-500 system connected to a conductimeter and according to the method described by the manufacturer Dionex. The result obtained makes it possible to calculate the amount of sulfates really bound to the EPS derivative, which is equal to the amount of total sulfates (obtained by elemental analysis) minus the amount of free sulfates (obtained by ion exchange chromatography).

Fourier transform infrared spectroscopy (FT-IR) was carried out on a Vector 22 having a resolution of 4 $cm^{-1}$. The infrared spectra of the polysaccharides were determined using KBr pellets (2 mg of polysaccharide are mixed with 200 mg of dry KBr), all the infrared spectra were recorded between 4000 and 400 $cm^{-1}$.

2.5. Results

Composition of an HE 800 DR Derivative:

| Characteristics | HE 800 DR derivative |
| --- | --- |
| Neutral monosaccharides (g/100 g)[1] | 0 |
| Acidic monosaccharides (g/100 g)[1] | 40 |
| Hexosamines (g/100 g)[1] | 40 |
| Total —$SO_3Na$ (g/100 g)[2] | 0 |
| Mc (g/mol)[4] | 15 000 |
| Mw (g/mol)[4] | 29 000 |
| Mn (g/mol)[4] | 13 000 |
| I (Mw/Mn)[4] | 2.2 |

[1]Colorimetric assays.
[2]Assay by elemental analysis.
[3]Assay by ion exchange chromatography.
[4]Determined by HPSEC chromatography in pullulan equivalents.

Composition of an EPS HE 800 DRS Derivative:

| Characteristics | HE 800 DRS derivative |
| --- | --- |
| Neutral monosaccharides (g/100 g)[1] | 0 |
| Acidic monosaccharides (g/100 g)[1] | 30 |
| Hexosamines (g/100 g)[1] | 30 |
| Total —$SO_3Na$ (g/100 g)[2] | 25 |
| Mc (g/mol)[4] | 4800 |
| Mw (g/mo1)[4] | 5800 |
| Mn (g/mol)[4] | 4500 |
| I (Mw/Mn)[4] | 1.3 |

[1]Colorimetric assays.
[2]Assay by elemental analysis.
[3]Assay by ion exchange chromatography.
[4]Detemined by HPSEC chromatography in pullulan equivalents.

Composition of an EPS HE 800 DRNS Derivative:

| Characteristics | HE 800 DRNS derivative |
| --- | --- |
| Neutral monosaccharides (g/100 g)[1] | 0 |
| Acidic monosaccharides (g/100 g)[1] | 20 |
| Hexosamines (g/100 g)[1] | 20 |
| Total —$SO_3Na$ (g/100 g)[2] | 34 |
| Mc (g/mol)[4] | 22 000 |
| Mw (g/mo1)[4] | 27 000 |
| Mn (g/mol)[4] | 19 000 |
| I (Mw/Mn)[4] | 1.4 |

[1]Colorimetric assays.
[2]Assay by elemental analysis.
[3]Assay by ion exchange chromatography.
[4]Determined by HPSEC chromatography in pullulan equivalents.

FIG. 1 shows the infrared spectra of the polysaccharide derivatives, before (HE 800 DR) and after the N-deacetylation reaction (HE 800 DRN). The FT-IR spectra in FIG. 1 were recorded on a Bruker Vector 22 spectrophotometer (resolution of 4 $cm^{-1}$). 2 mg of EPS HE 800 derivative were treated with 200 mg of KBr during the N-deacetylation step. The analysis of the infrared spectra of the derivatives, before and after the N-deacetylation step, shows, at the frequency of 1550 $cm^{-1}$, the loss of an absorption band characteristic of N-acetylated groups (FIG. 1).

Figure 2:
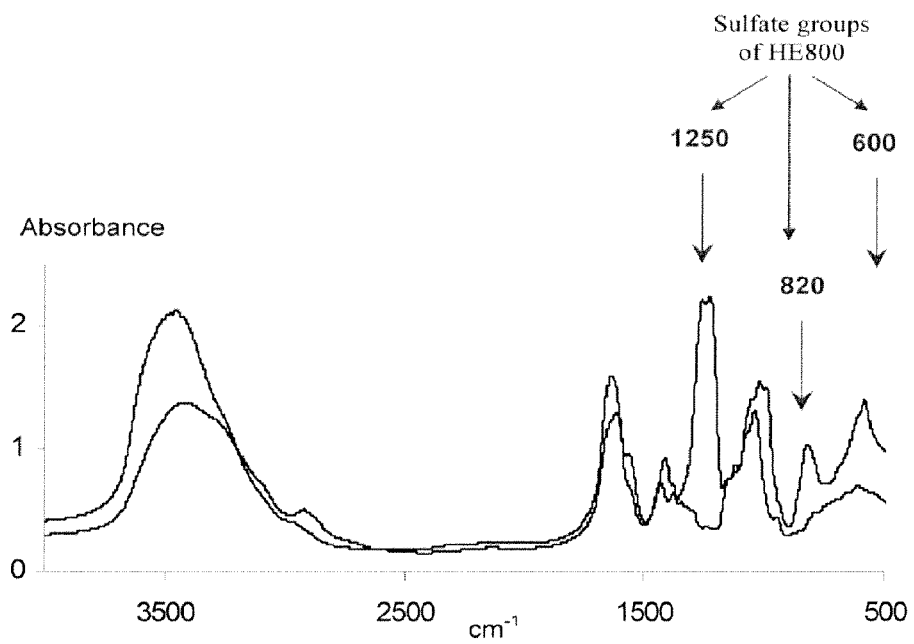
FIG. 2 represents the infrared spectra of the HE 800 derivative that has undergone a free-radical depolymerization (derivative HE 800 DR) or of the N-deacetylated and sulfated HE 800 derivative (HE 800 DRNS)

FIG. 2 shows the infrared (IR) spectra of the non-sulfated HE 800 polysaccharide derivative (HE 800 DR) and of the N-deacetylated and sulfated HE 800 polysaccharide derivative (HE 800 DRNS). The appearance of the bands corresponding to the presence of a sulfate ester (1250, 820 and 600 cm$^{-1}$) is observed for the polysaccharide derivative HE 800 DRNS.

EXAMPLE 3

Preparation of Derivatives According to the Invention Based on the Native EPS GY 785

(1) GY 785 DR corresponds to the low-molecular-weight polysaccharide derivative obtained after a depolymerization step.
(2) GY 785 DRS corresponds to the low-molecular-weight polysaccharide derivative obtained after a depolymerization step followed by a sulfation step.
1) Free-Radical Depolymerization and Reduction with Sodium Borohydride 400 mg of sulfated EPS GY 785 obtained above in the preceding step were dissolved in 95 ml of water. After dissolution, 2 ml of a catalytic solution containing 36 mg of copper acetate monohydrate ($10^{-3}$ M) were added. The temperature of the reactor is then brought to 60° C. and the pH is adjusted to 7.5 by the addition of 1 M sodium hydroxide. A 0.115% (v/v) solution of hydrogen peroxide was then added at a flow rate of 1 ml per minute, and the pH was regulated at around 7.5 by the addition of 1 M sodium hydroxide. The reaction was stopped after 1 hour.

The reduction is carried out at the end of depolymerization by the addition to the reactor of sodium borohydride (270 mg of NaBH$_4$ dissolved in 10 ml of water). The reduction is carried out with stirring for 2 hours at ambient temperature. The reduction is stopped by the addition of 10 N acetic acid, which makes it possible to eliminate the excess NaBH$_4$ remaining in the form of hydrogen gas that is given off. The solution was then filtered through a Büchner funnel with filters made of glass microfibers (porosity 3 µm). The filtered solution was eluted on a CHELEX® 20 column (BIORAD) in order to eliminate the residual copper. The decontaminated solution was then ultrafiltered through a cassette (cutoff threshold 1000 Da) and then lyophilized.
2) Chemical Sulfation of the EPS GY 785

500 mg of EPS GY 785 lyophilizate produced by the marine bacterium of hydrothermal origin *Alteromonas infernus* according to the process described in example 1 of patent FR 2 755 142, were dissolved in 100 ml of anhydrous DMF with gentle stirring (250 µm) for 2 hours at ambient temperature, and then for 2 hours at a temperature of 45° C.

When dissolution is complete, 2.5 g of pyridine-SO$_3$ complex sold under the reference 84737 by the company Fluka (i.e. 5 times the mass of the GY 785 polysaccharide) were added to the reaction medium. The temperature of the mixture was then brought to and maintained at 45° C. for 2 hours with stirring. The reaction mixture was transferred into a beaker. The reaction was then stopped by the addition of 40 ml of water, and the pH was then brought to 9 with 3 M sodium hydroxide. The reaction mixture was then dialyzed in a dialysis bag having a cutoff threshold of between 12 000 and 16 000 Da, against tap water (overnight with running water), and then 3 times for 24 hours against Milli-Q water.

After dialysis, the solution containing the sulfated EPS GY 785 was frozen and lyophilized.

The characteristics of the EPS DR and EPS DRS derivatives were determined according to the methods described above in example 1 and are summarized in the table below:

| Characteristics | EPS DR | EPS DRS |
|---|---|---|
| Total monosaccharides (g/100 g)[1] | 51 | nd |
| Acidic monosaccharides (g/100 g)[1] | 38 | nd |
| Total —SO$_3$Na (g/100 g)[2] | 10 | 42 |
| Mc (g/mol) | 7800 | 13 000 |
| Mw (g/mol) | 17 300 | 23 600 |
| Mn (g/mol) | 6000 | 8800 |
| I (Mw/Mn) | 2.8 | 2.7 |
| Anticoagulant activity[3] | inactive | 7 |

[1]Colorimetric assays.
[2]Assay by elemental analysis.
[3]Amount of polysaccharide in µg/ml of human plasma necessary to double the control coagulation time, ACT (control time = 40 seconds);
nd: not determined Composition of Another GY 785 DR Derivative:

| Characteristics | GY 785 DR derivative |
|---|---|
| Neutral monosaccharides (g/100 g)[1] | 40 |
| Acidic monosaccharides (g/100 g)[1] | 15 |
| Hexosamines (g/100 g)[1] | 0 |
| Total —SO$_3$Na (g/100 g)[2] | 10 |
| Mc (g/mol)[4] | 16 000 |
| Mw (g/mol)[4] | 40 000 |
| Mn (g/mol)[4] | 13 000 |
| I (Mw/Mn)[4] | 3 |

[1]Colorimetric assays.
[2]Assay by elemental analysis.
[3]Assay by ion exchange chromatography.
[4]Determined by HPSEC chromatography in pullulan equivalents.

Composition of Another GY 785 DRS Derivative:

| Characteristics | GY 785 DRS derivative |
|---|---|
| Neutral monosaccharides (g/100 g)[1] | 20 |
| Acidic monosaccharides (g/100 g)[1] | 10 |
| Hexosamines (g/100 g)[2] | 0 |
| Total —SO$_3$Na (g/100 g)[2] | 45 |
| Mc (g/mol)[4] | 23 000 |
| Mw (g/mol)[4] | 29 000 |
| Mn (g/mol)[4] | 21 000 |
| I (Mw/Mn)[4] | 1.4 |

[1]Colorimetric assays.
[2]Assay by elemental analysis.
[3]Assay by ion exchange chromatography.
[4]Determined by HPSEC chromatography in pullulan equivalents.

EXAMPLE 4

Preparation of Derivatives According to the Invention Based on the Native EPS HYD 721

(1) HYD 721 DR corresponds to the low-molecular-weight polysaccharide derivative obtained after a depolymerization step,
(2) HYD 721 DRS corresponds to the low-molecular-weight polysaccharide derivative sulfated by chemical sulfation according to the invention.

The sulfated HYD 721 polysaccharide derivative is obtained by carrying out the process described in example 2. However, since the native EPS HYD 721 does not contain N-acetylated hexosamines, the process for preparing the sulfated derivative does not comprise an N-deacetylation step.

Composition of an HYD 721 DR Derivative:

| Characteristics | HYD 721 DR derivative |
|---|---|
| Neutral monosaccharides (g/100 g)[1] | 68 |
| Acidic monosaccharides (g/100 g)[1] | 17 |
| Hexosamines (g/100 g)[1] | 0 |
| Total —SO$_3$Na (g/100 g)[2] | 11 |
| Mc (g/mol)[4] | 10 000 |
| Mw (g/mol)[4] | 12 000 |
| Mn (g/mol)[4] | 7000 |
| I (Mw/Mn)[4] | 1.7 |

[1]Colorimetric assays.
[2]Assay by elemental analysis.
[3]Assay by ion exchange chromatography.
[4]Determined by HPSEC chromatography in pullulan equivalents.

Composition of an HYD 721 DRS Derivative:

| Characteristics | HYD 721 DRS derivative |
|---|---|
| Neutral monosaccharides (g/100 g)[1] | 35 |
| Acidic monosaccharides (g/100 g)[1] | 5 |
| Hexosamines (g/100 g)[1] | 0 |
| Total —SO$_3$Na (g/100 g)[2] | 43 |
| Mc (g/mol)[4] | 17 500 |
| Mw (g/mol)[4] | 20 000 |
| Mn (g/mol)[4] | 10 000 |
| I (Mw/Mn)[4] | 2 |

[1]Colorimetric assays.
[2]Assay by elemental analysis.
[3]Assay by ion exchange chromatography.
[4]Determined by HPSEC chromatography in pullulan equivalents.

EXAMPLE 5

Effect of the Derivatives According to the Invention on the Proliferation of Dermal and Gingival Fibroblasts The sulfated polysaccharide derivatives used in the proliferation assays were prepared and characterized according to the protocols of examples 2 and 3.

5.1. Cells in Two-Dimensional Culture

The cells are seeded in two culture dishes at a rate of 10 000 cells per well, in Dulbecco's MEM Glutamax I culture medium containing 100 U/ml of penicillin, 100 μg/ml of streptomycin, 2 μg/ml of fungizone and supplemented with 10% of fetal calf serum (FCS).

After adhesion and spreading of the cells for 12 hours, the culture medium is replaced with a culture medium that may or may not be supplemented with various concentrations of a low-molecular-weight sulfated polysaccharide derivative: (i) the EPS GY 785 (GY 785 DRS) or (ii) the EPS HE 800 (HE 800 DRNS) HE 800. The cells are then counted after 2, 4, 7 and 10 days of culture. The controls correspond to cell cultures in the absence of derivatives in accordance with the invention (*).

Effect of the GY 785 DRS Derivative on the Proliferation of Dermal Fibroblasts in Two-Dimensional Culture:

| | Day 2 | Day 4 | Day 7 | Day 10 |
|---|---|---|---|---|
| Control* | 100 | 100 | 100 | 100 |
| 0.1 μg/ml GY 785 DRS | 94.5 | 100.0 | 145.3 | 151.4 |
| 1 μg/ml GY 785 DRS | 108.8 | 113.7 | 173.0 | 160.1 |
| 10 μg/ml GY 785 DRS | 87.6 | 157.3 | 156.9 | 151.2 |
| 100 μg/ml GY 785 DRS | 77.4 | 121.2 | 115.6 | 123.4 |

Effect of GY 785 DRS on the Proliferation of Gingival Fibroblasts in Two-Dimensional Culture:

| | Day 2 | Day 4 | Day 7 | Day 10 |
|---|---|---|---|---|
| Control* | 100 | 100 | 100 | 100 |
| 0.1 μg/ml GY 785 DRS | 112.0 | 121.8 | 135.0 | 139.1 |
| 1 μg/ml GY 785 DRS | 99.2 | 101.5 | 122.6 | 133.0 |
| 10 μg/ml GY 785 DRS | 90.2 | 124.3 | 160.4 | 183.3 |
| 100 μg/ml GY 785 DRS | 77.7 | 95.4 | 118.4 | 161.2 |

Effect of HE 800 DRNS on the Proliferation of Dermal Fibroblasts in Two-Dimensional Culture:

| | Day 2 | Day 4 | Day 7 | Day 10 |
|---|---|---|---|---|
| Control* | 100 | 100 | 100 | 100 |
| 10 μg/ml HE 800 DRNS | 109.00 | 159.96 | 157.70 | 146.56 |
| 100 μg/ml HE 800 DRNS | 95.49 | 191.12 | 163.60 | 167.60 |

The sulfated polysaccharide derivatives in accordance with the invention are capable of stimulating the proliferation of dermal and gingival fibroblasts in two-dimensional culture.

5.2. Reconstructed or Latticed Tissue (FIG. 3)

Reconstructed or latticed connective tissues consist of acid-soluble collagen type I fibers which, after neutralization, polymerize and form a gel containing fibroblasts. The preparation of a lattice is carried out under cold conditions in order to have better control of the polymerization of the collagen fibers.

This lattice under the influence of the cells will undergo numerous rearrangements that are noticeable in particular by virtue of its retraction, which is observed during the first two weeks of culture. This type of model makes it possible to study the behavior of the cells within an extracellular environment closer to the physiological environment than simple culturing on a dish.

Figure 3:
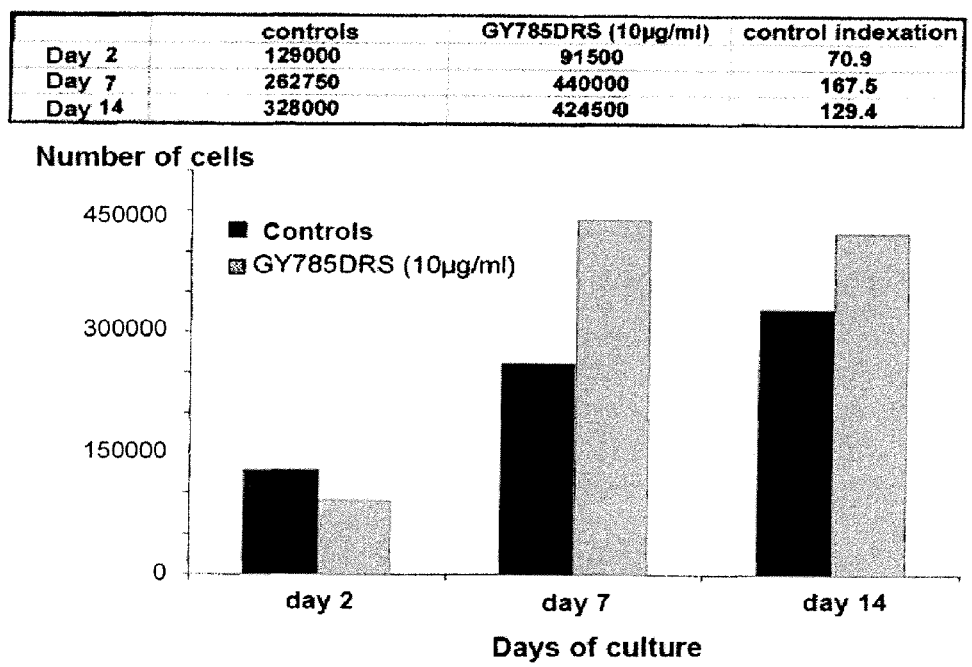
FIG. 3 is a graph which shows the effect of the free-radical depolymerized and then sulfated GY785 derivative, according to the invention, on the proliferation of fibroblasts in a reconstructed dermis.

FIG. 3 reveals that the low-molecular-weight sulfated polysaccharide derivative GY 785 DRS in accordance with the invention is capable, at the concentration of 10 μg/ml, of stimulating the proliferation of fibroblasts in reconstructed connective tissues.

EXAMPLE 6

Demonstration of the Effect of the Derivatives According to the Invention on the Selection of the Fibroblast Subpopulation As for the proliferation assays in two-dimensional cultures, the cells are seeded into culture dishes at a rate of 10 000 cells per well, in Dulbecco's MEM Glutamax I culture medium containing 100 U/ml of penicillin, 100 μg/ml of streptomycin, 2 μg/ml of fungizone and supplemented with 10% of fetal calf serum (FCS).

After adhesion and spreading of the cells for 12 hours, the culture medium is replaced with a culture medium that may or may not be supplemented with various concentrations of a sulfated derivative obtained from the EPS GY 785 (GY 785

DRS). The cultures are then fixed with alcohol after 2, 4, 7 and 10 days of culture, and the immunodetection on these cell cultures is carried out as follows:

The fixed cells are re-permeabilized in 70% ethanol (20 min), and then rehydrated in PBS (10 min). Endogenous peroxidases are blocked with a methanol (30%), $H_2O_2$ (0.3%) solution. This process is followed by rinsing with PBS (2 min) then blocking of the nonspecific antigenic sites with a PBS/1% skimmed milk solution (1 h). The cultures are then incubated with a primary antibody (mouse IgG) directed against human α-actin (1/30; 50 min) and then rinsed with PBS (3×10 min). The cells are then incubated, in the dark for 60 min, with a biotinylated anti-mouse IgG antibody (1/200), rinsed with PBS (3×10 min), and then incubated with peroxidase-coupled streptavidin (1/200).

After rinsing (PBS 3×10 min), the visualization of the peroxidase activity with 3,3'-diaminobenzidine is carried out in a Tris/HCl buffer (100 mM, pH 7.2-7.4) containing 0.1% of $H_2O_2$ (15 min, in the dark). The peroxidase activity reveals a brown fibrillar material that corresponds to the α-actin microfilaments in the cytoplasm of the positive cells. The products used come from the company DAKO under the name DAKOImmuno-detection.

Figure 4:
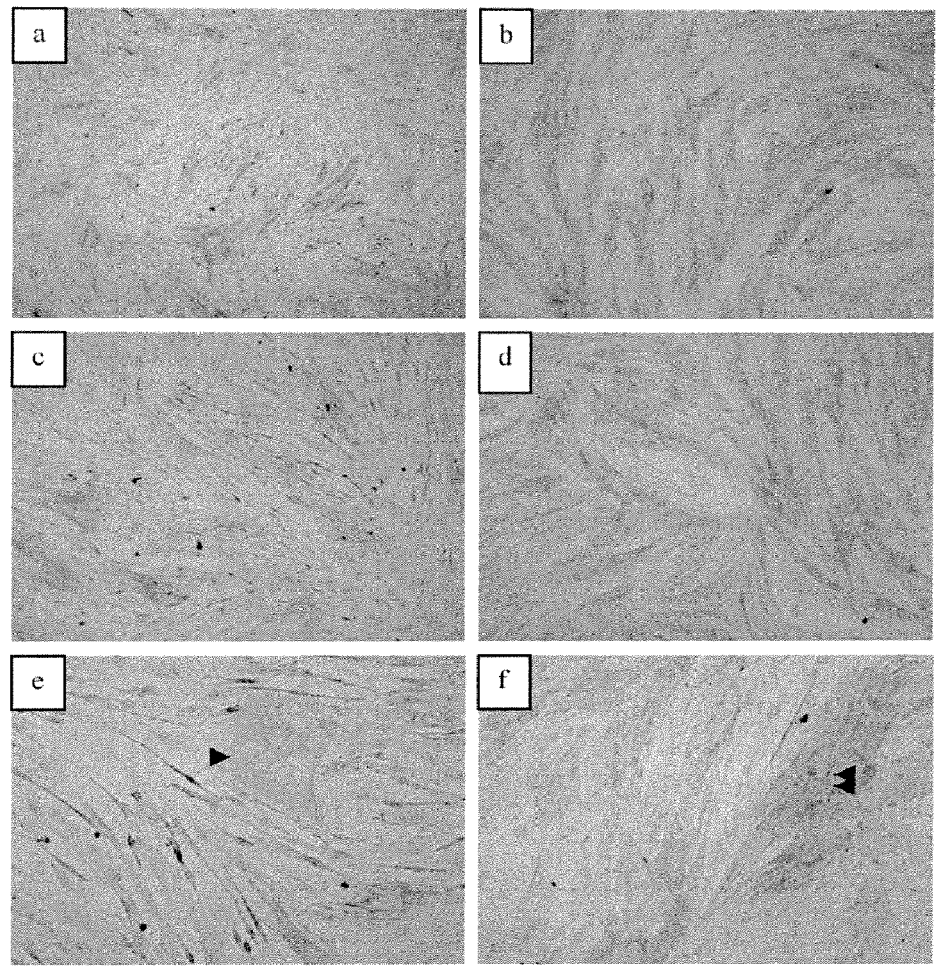
FIG. 4 is a set of 6 photographs a, b, c, d, e and f. This figure relates to an immunodetection test, in a dermal fibroblast culture, of α-actin filaments that are characteristic of the myofibroblast subpopulation.

FIG. 4 demonstrates that the low-molecular-weight sulfated polysaccharide derivative GY 785 DRS in accordance with the invention is capable of stimulating the proliferation of fibroblasts to the detriment of myofibroblasts. Photographs a, c and e correspond to cultures supplemented with 10 μg/ml of sulfated derivative, in which the dominant population is made up of fibroblasts to the detriment of myofibroblasts. Photographs b, d and f correspond to control cultures without sulfated derivative, in which numerous myofibroblasts are visible.

The control cultures not treated with the derivatives in accordance with the invention comprise a large number of myofibroblasts (α-actin-positive), while fibroblasts not expressing α-actin form the dominant cell type in the treated cultures.

EXAMPLE 7

Effect of the Derivatives According to the Invention on the Secretion of Matrix Proteases 7.1. Protocol The cells are seeded into culture dishes at a rate of 40 000 cells per well and are brought to confluence in Dulbecco's MEM Glutamax I culture medium containing 100 U/ml of penicillin, 100 μg/ml of streptomycin, 2 μg/ml of fungizone and supplemented with fetal calf serum (FCS).

At confluence, the culture medium is replaced with medium that does not contain any FCS and may or may not be supplemented with IL-1β at a final concentration of 100 U/ml, in the presence or absence of sulfated derivatives.

The culture media are sampled after 48 hours, in order to study the MMP secretion by the fibroblasts, by zymography or by Western blotting. For each experimental condition carried out in quadruplicate, two wells are fixed with ethanol and the other two are trypsinized in order to detach the cells so as to count them.

The metalloprotease secretion is detected and quantified by zymography. It is a particularly sensitive method based on SDS-PAGE electrophoresis carried out under reducing conditions. The MMP-2 substrate, gelatin, copolymerizes with the acrylamide. After migration, the SDS is eliminated by washing in a solution of Triton X-100, allowing restoration of the MMP-2 activity. The gel is then incubated at 37° C. in an incubation buffer (0.1 M Tris/HCl, pH 7.4, 30 mM $CaCl_2$, 0.001% $NaN_3$, 0.0015% Brij, 0.1 μm $ZnCl_2$).

After staining (coomassie blue (0.5%), acetic acid (10%), isopropanol (30%)), and then destaining (acetic acid (10%), methanol (40%), distilled water (50%)), the bands illustrating the MMP-2 metalloprotease activity appear destained. The shade of gray and the surface area of these bands are quantified on an image analyzer, the [(shade of gray×surface area)/number of cells] ratio allows a quantification of the gelatinolytic activities and comparison between the control cultures and the cultures containing the exopolysaccharide.

7.2. Effect of HE 800 DRNS on the Secretion of MMP-2 by Fibroblasts in Culture, Result Obtained by Zymography (FIG. 5)

Figure 5:
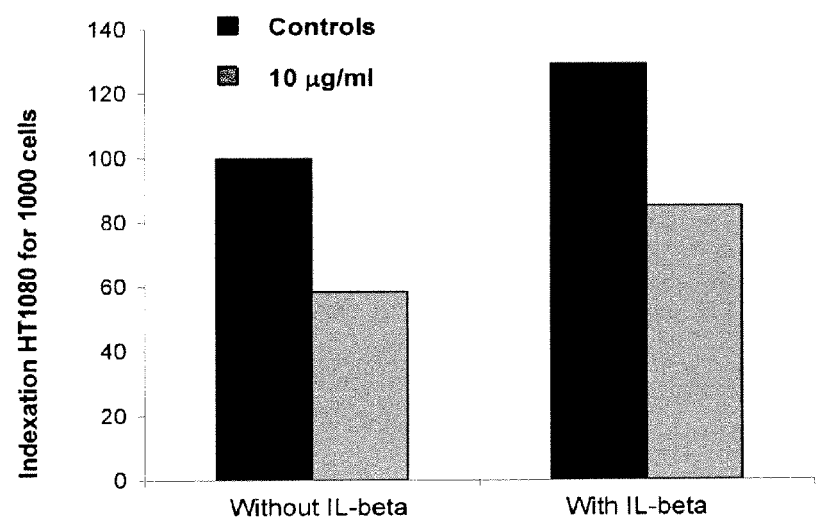
FIG. 5 is a graph which reflects a result obtained by zymography, and shows the effect of HE 800 DRNS on the secretion of MMP-2 by fibroblasts in culture.

The graph in FIG. 5 shows that the MMP-2 secretion is inhibited when the fibroblasts are cultured in the presence of low-molecular-weight sulfated polysaccharide derivatives, in the presence or absence of IL1β.

7.3. Effect of HE 800 DRNS on the Secretion of Stromelysin 1 (MMP-3) by Fibroblasts in Culture, Result Obtained by Western Blotting (FIG. 6)

Figure 6:
FIG. 6 is a set of two photographs, a and b, which show the effect of a derivative in accordance with the invention on the secretion of a matrix protease, stromelysin (MMP-3).

FIG. 6 shows that the addition of HE 800 DRNS greatly decreases the secretion of MMP-3 by the fibroblasts, whether this secretion is baseline (photograph a) or induced by an inflammatory cytokine IL-1β (photograph b). Photograph (a) shows confluent fibroblasts incubated for 48 h in a serum-free medium (lane 1), and in a serum-free medium containing 10 μg/ml of EPS derivative (lane 2); photograph (b) shows confluent fibroblasts incubated for 48 h in a serum-free medium containing 100 U/ml of IL-1β (lane 1), and in a serum-free medium containing 10 μg/ml of EPS derivative and 100 U/ml of IL-1β (lane 2).

1: control=untreated culture
2: culture treated with 100 U/ml of HE 800 DRNS.

In conclusion, the sulfated polysaccharide derivatives in accordance with the invention are capable of inhibiting the secretion of matrix proteases, gelatinase A (MMP-2) and stromelysin 1 (MMP-3), by fibroblasts in two-dimensional cultures.

EXAMPLE 8

Effect of the Derivatives According to the Invention on Complement 8.1 Principle Complement can be activated by 3 different activation pathways: the conventional pathway, the alternative pathway and the mannose-binding lectin (MBL) pathway resulting, via different mechanisms, in the formation of enzymes having identical substrates: the C3/C5 convertases capable of activating C3 and C5. The activation reactions take place as a cascade: one component acquires an enzymatic activity that induces the activation of the next component, and so on.

Insofar as the final activation of complement is common to the three pathways, only the conventional pathway is studied in this example. The activation of the conventional pathway occurs when the C1 complex interacts with antigen-antibody complexes or immune aggregates containing IgGs or IgMs. The system used to study the conventional pathway is based on the complement activation by an immune complex consisting of rabbit antibody-coated sheep red blood cells. The rabbit antibodies having recognized as foreign the red blood cells, in the presence of human serum, trigger mainly the activation of the conventional pathway. This activation leads to the formation of C3 convertase, which then triggers the activation of the alternative pathway. The activation of these two pathways results in the formation of a membrane attack complex at the surface of the red blood cells. This complex induces rupturing of the red blood cells and the release of hemoglobin. The activation of the complement system is measured by assaying the amount of hemoglobin released, by measuring the spectrophotometric absorption at 414 nm. The activator (sheep red blood cells) is also used as a revealer of the activation by virtue of the hemoglobin released during the cell lysis. The dilution of the human serum is adjusted for a given amount of blood cells, such that 50% of the cells are lysed.

The antibody-coated red blood cells are incubated in the absence (control) and in the presence of various sulfated polysaccharide derivatives. The amount of hemoglobin released decreases (decrease in the absorption at 414 nm), reflecting a decrease in the number of red blood cells lysed and an inhibitory effect of the sulfated polysaccharide derivatives on the activation of the conventional complement pathway.

350 µl of normal human serum (NHS) (diluted to 1/100th in VBS2+ buffer) are incubated with 450 µl of VBS2+, and 200 µl of rabbit antibodies ($10^8$ cells/ml), in the presence or absence of sulfated polysaccharide derivatives. After an approximate reaction time of 45 min at 37° C., a solution of cold NaCl (0.15 M) is added and the cells are centrifuged at 2400 rpm for 10 min. The absorption of the supernatants is measured at 414 nm.

8.2. Result
Percentages of Complement Inhibition (Conventional Pathway) in the Presence of Various Amounts of EPS Derivatives GY 785 DRS and HE 800 DRNS:

| | Amount of derivatives | | | |
|---|---|---|---|---|
| Percentage inhibition | 0.5 µg | 2.5 µg | 5 µg | 10 µg |
| GY785DRS | 42 | 100 | 100 | 100 |
| GY785DR | 0 | 0 | 0 | 0 |
| | 1 µg | | 5 µg | 10 µg |
| HE800DRNS | 18 | | 38 | 48 |
| HE800DR | 0 | | 0 | 0 |

The low-molecular-weight sulfated polysaccharide derivatives in accordance with the invention are capable of inhibiting the conventional complement pathway.

EXAMPLE 9

Effect of the Derivatives According to the Invention on the Proliferation of Medullary Cells Intended to Become Mesenchymal Cells 9.1. Protocol
Stromal cells are obtained from ground bone marrow material, and this ground material is centrifuged so as to recover a cell pellet. The cells are resuspended in culture medium made up, for 500 ml, of medium containing 10% of horse serum, 10% of fetal calf serum, 200 nM L-glutamine (4 ml), 100× MEM vitamin (Gibco brl) (4 ml), 7.5% $Na_2HCO_3$ (4 ml), 50× essential amino acids with L-glutamine (Gibco brl) (4 ml), 100× sodium pyruvate (4 ml), 100× nonessential amino acids (Gibco brl) (1.6 ml), the whole being diluted in a 1× McCoy's medium (Gibco brl).

After 24 hours of culture, only the cells having adhered to the bottom of the dish are kept.

The proliferation assays are carried out under the same conditions as those described for the proliferation assays on the cultures of human gingival and dermal fibroblasts. The cell countings are carried out after 2, 4, 7 and 10 days of culture. The immunodetections directed against certain phenotypic markers (see α-actin protocol) showed that these cells do not express a marker characteristic of macrophages, CD68; a minority of these cells express a leukocyte marker, CD45, but, on the other hand, they express a cyto-skeletal protein characteristic of mesenchymal cells, vimentin. Moreover, some of these cells are capable of expressing, without stimulation, collagen type I and collagen type III, which are characteristic of mesenchymal cells in culture.

9.2. Result
Effect of GY 785 DRS on the Proliferation of Medullary Cells Intended to Become Mesenchymal Cells:

| | Day 2 | Day 4 | Day 7 | Day 10 |
|---|---|---|---|---|
| Control (culture without derivatives) | 100 | 100 | 100 | 100 |
| 0.1 µg/ml GY 785 DRS | 93.6 | 129.4 | 127.8 | 130.4 |
| 1 µg/ml GY 785 DRS | 95.5 | 170.3 | 170.0 | 164.8 |
| 10 µg/ml GY 785 DRS | 79.2 | 134.5 | 155.9 | 179.8 |
| 100 µg/ml GY 785 DRS | 86.2 | 129.3 | 139.4 | 167.9 |

The proliferation of the medullary cells intended to become mesenchymal cells is greatly stimulated in the presence of the EPS GY 785 DRS.

What is claimed is:

1. A method for selectively stimulating the proliferation of adult mesenchymal stem cells, comprising a step of:
   contacting a cell sample comprising adult mesenchymal stem cells with a low-molecular-weight sulfated polysaccharide derivative,
   wherein said low-molecular-weight sulfated polysaccharide derivative:
      is a derivative of a marine native exopolysaccharide (EPS) excreted by a marine bacterium of the *Alteromonas* genus or *Pseudoalteromonas* genus or *Vibrio* genus;
      has a molecular weight of less than or equal to 25,000 g/mol, a polydispersity index of less than or equal to 2 and a degree of sulfate group substitution between 10% and 45% by weight inclusive, and
      is obtained by a process comprising:
   a step consisting of free-radical depolymerisation of said native EPS so as to obtain a depolymerized derivative of low molecular weight, less than or equal to 100,000 g/mol, and
   a subsequent step consisting of sulfation of the depolymerized derivative, comprising adding to the depolymerised derivative at least one sulfation agent in an amount sufficient to obtain a sulfated polysaccharide derivative having a degree of sulfate group substitution of between 10% and 45% by weight relative to the total weight of the sulfated polysaccharide derivative.

2. The method according to claim 1, wherein the process by which the low-molecular-weight sulfated polysaccharide derivative is obtained further comprises at least one of:
   lyophilization of the depolymerized derivative prior to sulfation,
   reduction of the depolymerized derivative prior to sulfation,
   N-deacetylation of the depolymerized derivative prior to sulfation, lyophilization of the sulfated polysaccharide derivative following sulfation, N-deacetylation of the sulfated polysaccharide derivative following sulfation, dialysis of the sulfated polysaccharide derivative following sulfation, and any combination thereof.

3. The method according to claim 1, wherein the free-radical depolymerization is carried out by adding to the native EPS a solution of an oxidizing agent selected from the group consisting of peroxides and peracides, in the presence of a metal catalyst selected from the group consisting of $Cu^{2+}$, $Fe^{2+}$, $Cr^{3+}$ and $Cr_2O_7^{2-}$.

4. The method according to claim 3, wherein said oxidizing agent is a solution of hydrogen peroxide having a concentration of between 0.1% and 0.5% by weight, and wherein the solution of hydrogen peroxide is added at a flow rate of between V1/1000 and V1/10 ml/minutes, V1 being the volume of the reaction medium containing the native EPS to which the solution of hydrogen peroxide is added.

5. The method according to claim 1, wherein the at least one sulfation agent is selected from the group consisting of complexes of pyridine sulfate, complexes of triethylamine sulfate, complexes of dimethylformamide sulfate and complexes of trimethyl sulfate.

6. The method according to claim 1, wherein the at least one sulfation agent is added in a weight amount representing from 4 to 6 times the mass of the depolymerized derivative and is added to the depolymerized derivative which is in dry form or in solution in an anhydrous solvent.

7. The method according to claim 1, wherein the bacterium of the *Alteromonas* genus or *Pseudoalteromonas* genus belongs to a strain selected from the group consisting of strains GY785, HYD 657, HYD 708, HYD 721, HYD 1545, HYD 1644, ST 716 and MS 907, and the bacterium of the *Vibrio* genus belongs to the HE800 strain.

8. The method according to claim 1, wherein said native EPS excreted by a marine bacterium of the *Alteromonas* genus or *Pseudoalteromonas* genus has an osidic composition comprising: from 20% to 70% by weight of neutral monosaccharides, from 5% to 60% by weight of acidic monosaccharides, and from 0% to 1% by weight of amino sugars.

9. The method according to claim 8, wherein said native EPS has an osidic composition comprising: from 30% to 60% by weight of neutral monosaccharides, from 6% to 50% by weight of acidic monosaccharides, and from 0% to 1% by weight of amino sugars.

10. The method according to claim 9, wherein said native EPS has an osidic composition comprising: from 38% to 57% by weight of neutral monosaccharides, from 8% to 42% by weight of acidic monosaccharides, and from 0% to 1% by weight of amino sugars.

11. The method according to claim 1, wherein said native EPS excreted by a marine bacterium of the *Vibrio* genus has an osidic composition comprising: from 0% to 5% by weight of neutral monosaccharides, from 20% to 50% by weight of acidic monosaccharides, from 20% to 50% by weight of amino sugars, and from 0% to 15% by weight of N-acetylated groups.

12. The method according to claim 11, wherein said native EPS has an osidic composition comprising: from 0% to 1% by weight of neutral monosaccharides, from 25% to 40% by weight of acidic monosaccharides, from 25% to 40%, by weight of amino sugars, and from 4% to 8% by weight of N-acetylated groups.

13. The method according to claim 12, wherein said native EPS has an osidic composition comprising: from 0% to 1% by weight of neutral monosaccharides, from 30% to 32% by weight of acidic monosaccharides, from 30% to 35% by weight of amino sugars, and from 5% to 6% by weight of N-acetylated groups.

14. The method according to claim 1, wherein said native EPS has a protein content of from 0% to 15% by weight, or from 0% to 5% by weight, or from 0% to 1% by weight.

15. The method according to claim 1, wherein the cell sample comprises a heterogeneous population of cells and wherein the low-molecular-weight polysaccharide derivative stimulates the proliferation of adult mesenchymal stem cells to the detriment of any other cell population.

16. The method according to claim 15, wherein contacting the cell sample with a low-molecular-weight polysaccharide derivative comprises:

contacting and culturing the cell sample with the low-molecular-weight sulfated polysaccharide derivative to obtain a cell sample enriched in adult mesenchymal stem cells;

separating the adult mesenchymal stem cells from the enriched cell sample; and amplifying the separated adult mesenchymal stem cells.

17. The method according to claim 1 or claim 15, wherein the adult mesenchymal stem cells obtained are implanted into a subject.

18. The method according to claim 17, wherein, within the subject, the adult mesenchymal stem cells differentiate into fibroblasts, chondrocytes, osteoblasts, adipocytes or muscle cells depending on the tissue in which they were implanted.

* * * * *